United States Patent
Zuk

(10) Patent No.: US 7,047,978 B2
(45) Date of Patent: May 23, 2006

(54) BRUXISM APPLIANCE AND METHOD OF FORMING

(76) Inventor: Michael Yar Zuk, 102 Allison Crescent, Red Deer, Alberta (CA) T4R 2G9

( * ) Notice: Subject to any disclaimer, the term of this patent is extended or adjusted under 35 U.S.C. 154(b) by 804 days.

(21) Appl. No.: 09/758,133

(22) Filed: Jan. 12, 2001

(65) Prior Publication Data
US 2001/0017136 A1  Aug. 30, 2001

(51) Int. Cl.
*A61F 5/56* (2006.01)
(52) U.S. Cl. .................. 128/848; 128/859; 128/861; 128/862; 602/902
(58) Field of Classification Search ............ 128/846, 128/848, 859–862; 433/6, 213, 68, 215
See application file for complete search history.

(56) References Cited

U.S. PATENT DOCUMENTS

| 3,768,164 | A | * | 10/1973 | Breads ........................... 32/2 |
| 3,813,781 | A | * | 6/1974 | Forgione .................... 433/68 |
| 4,557,692 | A | | 12/1985 | Chorbajian |
| 4,955,393 | A | * | 9/1990 | Adell ......................... 128/859 |
| 5,911,576 | A | * | 6/1999 | Ulrich et al. ............... 433/68 |
| 6,077,075 | A | * | 6/2000 | Bedard ....................... 433/213 |

\* cited by examiner

*Primary Examiner*—Michael A. Brown
(74) *Attorney, Agent, or Firm*—Hicks & Penman Ltd.

(57) ABSTRACT

A bruxism appliance and a method of forming a bruxism appliance is described for providing a patient and a dentist with a visual indication of the degree of bruxism by the patient. The invention teaches the application of an abradable composition to the non-retaining/opposing dentition contacting surfaces of the appliance in order that specific wear patterns can be observed on the appliance following use by a patient.

3 Claims, 2 Drawing Sheets

BRUXISM APPLIANCE AND METHOD OF FORMING

FIELD OF THE INVENTION

A bruxism appliance and a method of forming a bruxism appliance is described for providing a patient and a dentist with a visual indication of the degree of bruxism by the patient. The invention teaches the application of an abradable composition to the non-retaining/opposing dentition contacting surfaces of the appliance in order that specific wear patterns can be observed on the appliance following use by a patient.

BACKGROUND OF THE INVENTION

Bruxism or grinding of the teeth is defined as rhythmic or spasmodic grinding of the teeth in other than chewing movements of the mandible, especially such movements performed during sleep. Dental malocclusion and tension-release factors are the usual inciting causes (Dorland's Illustrated Medical Dictionary, 26$^{th}$ edition, W.B. Saunders Co.). It is a significant dental problem afflicting upwards of 30% of the population. As bruxism normally occurs at night and damage to the teeth from bruxism occurs slowly, most patients are unaware of the problem and only notice the damage to their teeth after significant wear has occurred. If left untreated bruxism will slowly result in severe wear of the dentition, cracks and fractures in the teeth and may result in premature tooth loss.

The canine teeth are designed to be protective of the rest of the dentition by their large crown, root morphology and position. The reduction of the protective length of these teeth is commonly the first visible sign that bruxism has occurred. Large well developed masseter muscles are also a feature of severe bruxers. Apart from these indications, bruxers do not often exhibit symptoms such as pain and, as such, it is often difficult for a dentist to convince a patient that a significant problem exists, let alone suggest an appropriate method for prevention.

In treating bruxism, most patients will often not respond to various forms of treatment such as bite or occlusal adjustments and orthodontics. Therefore, as they are unable to consciously prevent the damaging activity from occurring, a bruxism appliance, which forms a physical and softer barrier to grinding teeth, is often the only form of treatment that prevents further damage from occurring.

Bruxism appliances are routinely prescribed to patients at various stages of dental wear as well as after cosmetic dentistry procedures that have replaced the worn teeth from this disorder.

The use of bruxism appliances also presents particular problems as a large percentage of patients when fitted with appliances discontinue the use of their appliances, often because it is difficult to know whether they are still bruxing.

Accordingly, there has been a need for a bruxism appliance and a method of treating a bruxism appliance in order to physically show a patient the degree of grinding they perform and the wear patterns in order to assist in convincing a patient to continue with use of the appliance, or alternatively demonstrate that use of the appliance is no longer required.

In particular, there has been a need for a bruxism appliance and method of treating a bruxism appliance that provides a long-term quantitative indication of the degree of bruxism for subsequent treatments.

A review of the prior art reveals that such a system has not been developed. For example, U.S. Pat. No. 4,557,692 discloses an occlusal splint appliance having a softer inner layer. This reference does not teach the application of an abradable layer to the appliance. Other existing methods involve using multi-coloured plastics for sports mouth guards that are fabricated in the laboratory. These coloured materials are employed for cosmetic purposes only and do not serve any diagnostic purpose. Furthermore, such systems do not allow the dentist to have precise control of the surface thickness as often the surface must be adjusted by the dentist to accommodate the biting surfaces of the opposing teeth. Other methods involve applying easily-removed dyes to the surface to mark the bite of the opposing teeth, which thereby allow the dentist to see the contact areas. These high contact areas are adjusted to create a balanced biting surface. The surface colour is then removed prior to delivery to and use by the patient. Neither of these methods or appliances provide the dentist and patient with an on-going indication of bruxism and its effects.

SUMMARY OF THE INVENTION

In accordance with the invention, there is provided a bruxism appliance comprising a molded polymeric base for placement and fitting to a patient's upper or lower dentition, the molded polymeric base including an abradable overlayer applied after fitting the molded polymeric base to the upper or lower dentition the overlayer being a different colour to the polymeric base whereby use of the appliance by a patient indicates the degree of bruxism by the patient by abrasion of the overlayer.

In further embodiments of the invention, the molded polymeric base is selected from any one of or a combination of acrylic resin or plastic and/or the abradable overlayer is selected from any one of or a combination of an acrylic resin, natural resin or composite.

In one embodiment the overlayer has a hardness softer than the molded polymeric base.

In a specific embodiment, the overlayer includes an acrylic resin blended with a titanium oxide pigment. In a still further embodiment, a pH indicator is bound to the appliance for indicating the pH of a patient's mouth during use of the appliance wherein the pH indicator can be incorporated into the abradable overlayer or chemically or mechanically fixed to the appliance.

In another form of the invention, there is provided a method of coating a bruxism appliance comprising the steps of:

(a) fitting a bruxism appliance having a polymetric base to a patient's upper and lower dentition; and, (b) applying an abradable overlayer to the polymetric base by any one of or a combination of painting or spraying where the abradable overlayer is selected from any one of or a combination of an acrylic resin, natural resin or composite material.

In a still further form, the invention provides a kit for applying an abradable overlayer to a polymeric base of a bruxism appliance, the kit comprising a packaged amount of a liquid abradable overlayer composition and an applicator wherein the overlayer composition and an applicator brush contained within a sterile package.

In further embodiments of the kit, the applicator is selected from a brush or a spray container and/or the abradable overlayer is selected from any one of or a combination of an acrylic resin, natural resin or composite material.

DESCRIPTION OF THE DRAWINGS

These and other features of the invention are described with reference to the drawings wherein.

DETAILED DESCRIPTION OF THE INVENTION

With references to the figures, a bruxism appliance 10 and method of treating a bruxism appliance is described.

A bruxism appliance 10 having a polymeric base 12 is fitted to a patient's teeth as in known in the art by initially adjusting the appliance to fit comfortably and occlude evenly against the opposing dentition. This process may require spot grinding with a slow speed hand tool and the use of articulating paper. After proper fitting, the appliance would otherwise be cleaned for delivery to the patient. A bruxism appliance 10 having a polymeric base 12 is preferably manufactured from an acrylic resin.

In accordance with the invention, a coating 14 is applied to the opposing teeth contacting surfaces of the polymeric base 12 to a desired thickness by hand brushing, spray painting or dipping. Typically, this thickness is sufficient to fully coat the desired surfaces of the appliance but not overly thick so as to affect the fit of the appliance. The coating 14 is allowed to dry or cure as appropriate for the specific composition.

Suitable coatings include non-toxic resins, such as an acrylic resin, having a hardness which may be slightly higher, equal to or slightly less than the underlying appliance or other suitable compositions which effectively cross-link to the appliance.

Figure 1:
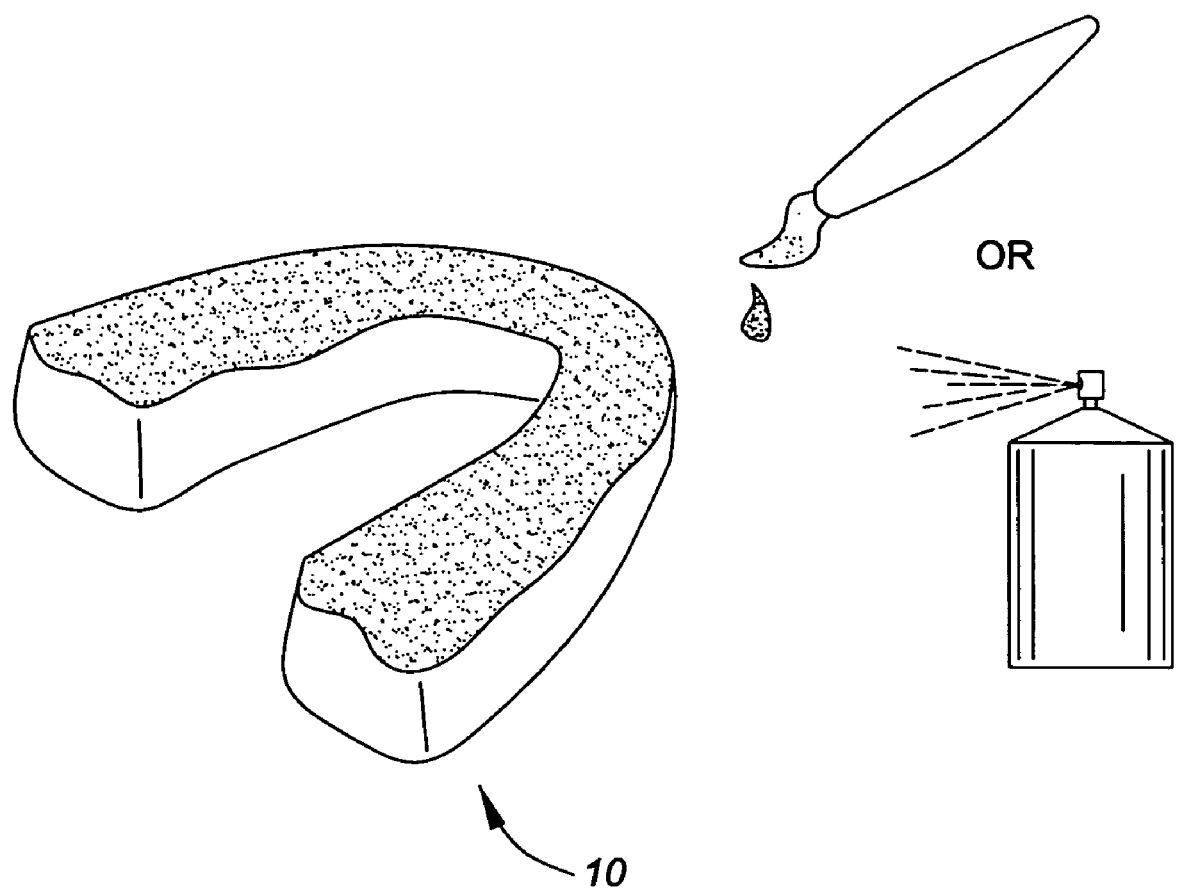
FIG. 1 is a sketch of the coating procedure involving spraying or painting the bruxism appliance with a composition in accordance with the invention.
Figure 2:
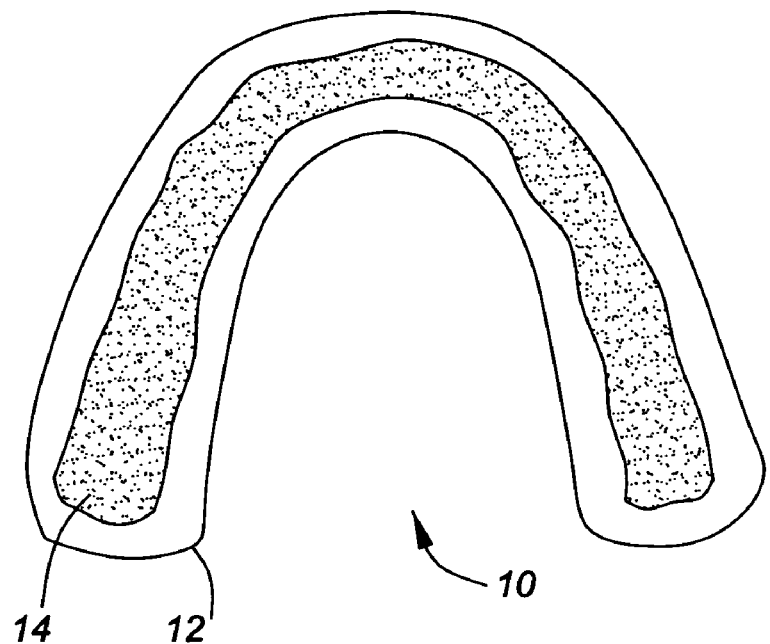
FIG. 2 is a photograph of a coated appliance in accordance with the invention.

Preferred coatings are those which are a contrasting colour to the underlying base of the appliance allowing the dentist and patient a clear indication of the specific bruxism patterns. It is also preferred that the coating does not chemically react with, stain or leave flecks of material on a patient's teeth upon removal of the appliance. Titanium oxide as a pigment in an acrylic resin solution has provided positive results. An example of a coated appliance is shown in FIG. 2.

The appliance is delivered to the patient with instructions concerning its use. After using the coated appliance for a period of time determined by the dentist, the patient returns the device to the dentist for an evaluation of the degree of bruxism thereby allowing the dentist to diagnose the relative need for either continued use or discontinued use of the appliance. As well, the patient is also able to visually evaluate their need to continue using the device.

Figure 3:
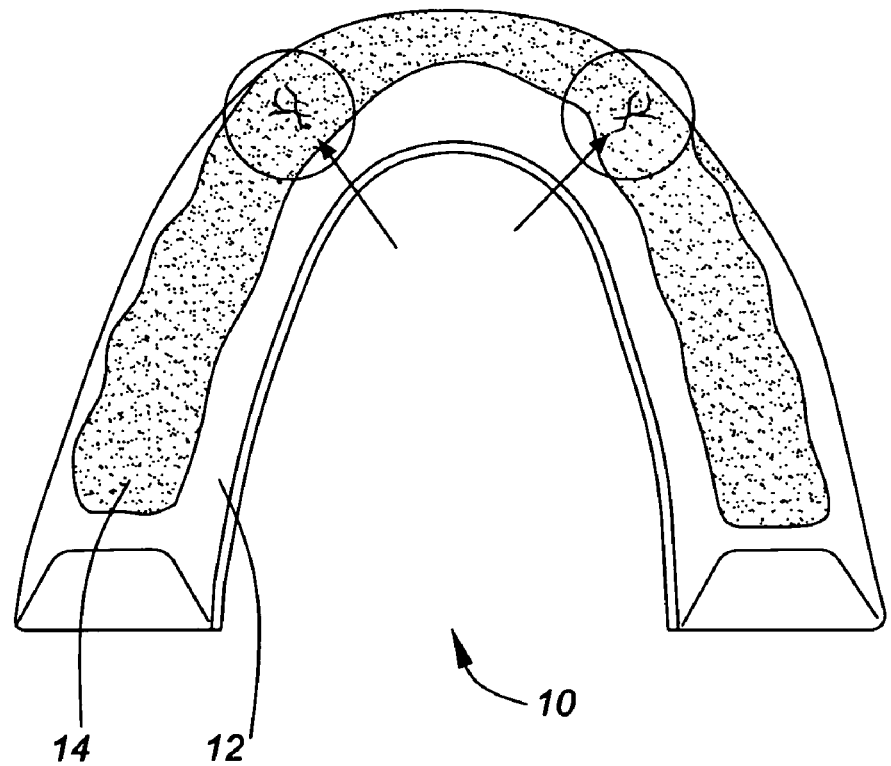
FIG. 3 is a photograph of a coated appliance which has been worn.

More specifically, the dentist is able to identify specific grinding/clenching patterns. For example, vertical grinders clench with little side movement whereas horizontal grinders grind side to side and produce the most damage. There are also anterior-posterior grinders which primarily damages the front teeth. By identifying the grinding pattern, the dentist will be able to adjust the occlusal fit with selective grinding so that contact is even on both sides of the appliance. FIG. 3 is an example of a used appliance where the grinding pattern is revealed.

The use of a bruxism appliance may also cause a patient to stop a grinding habit or otherwise reduce the damage to the teeth, dental restorations, supporting structures and the temporomandibular joint.

In a preferred embodiment, the coating composition and applicator are provided to the dentist in a single-use kit form in order to reduce the risks of cross-contamination which might otherwise occur. In this embodiment, an applicator and the composition would be provided in a sterilized package.

In another embodiment, the coating solution is provided in a sprayable solution form which also reduces the risk of cross-contamination.

In a still further embodiment, the composition is provided with a pH indicator in order to provide the dentist with an indication of the degree of acid reflux by a patient during appliance use and in particular at night. A comparison of the degree of wear of the appliance in combination with a determination of the typical pH of the mouth, will assist in diagnosing both the degree of bruxism and acid-reflux in the patient.

In one embodiment, the pH indicator is incorporated into the applied coating wherein a colour change of the coating would provide an indication of the acidity in the oral cavity from stomach acids.

Alternatively, a separate pH indicator is affixed to the appliance by an appropriate bonding agent or design of the appliance. That is, known pH indicators, such as pH papers may be chemically bound to the appliance or mechanically retained against the appliance. In this embodiment, the lowest pH achieved in the mouth would be determined by comparing the pH indicator against a colour standard as is known.

The invention claimed is:

1. A bruxism appliance comprising a molded polymeric base for placement and fitting to a patient's upper or lower dentition, the molded polymeric base including an abradable overlayer applied after fitting the molded polymeric base to the upper or lower dentition, the overlayer being a different colour to the polymeric base whereby use of the appliance by the patient indicates the degree of bruxism by the patient by abrasion of the overlayer, wherein the overlayer has a hardness softer that the molded polymeric base, and wherein the overlayer includes an acrylic resin blended with a titanium oxide pigment.

2. A bruxism appliance comprising a molded polymeric base for placement and fitting to a patient's upper or lower dentition, the molded polymeric base including an abradable overlayer applied after fitting the molded polymeric base to the upper or lower dentition, the overlayer being a different colour to the polymeric base and selected from any one of or a combination of acrylic resin, natural resin, or composite, whereby use of the appliance by the patient indicates the degree of bruxism by the patient by abrasion of the overlayer, further comprising a pH indicator bound to the appliance for indicating the pH of a patient's mouth during use of the appliance.

3. A bruxism appliance as in claim 2 wherein the pH indicator is incorporated into the abradable overlayer or is chemically or mechanically fixed to the appliance.

* * * * *